(12) United States Patent
Santar et al.

(10) Patent No.: US 6,743,775 B2
(45) Date of Patent: Jun. 1, 2004

(54) SLOW RELEASE FORMULATIONS COMPRISING ANIONIC POLYSACCHARIDE

(75) Inventors: Ivan Santar, Predklasteri (CZ); Frantisek Kiss, Brno (CZ); Jiri Briestensky, Cernilov (CZ)

(73) Assignee: Alpenstock Holdings Limited, Sallynoggin (IE)

( * ) Notice: Subject to any disclaimer, the term of this patent is extended or adjusted under 35 U.S.C. 154(b) by 512 days.

(21) Appl. No.: 09/764,348

(22) Filed: Jan. 19, 2001

(65) Prior Publication Data

US 2001/0006957 A1 Jul. 5, 2001

Related U.S. Application Data

(63) Continuation of application No. PCT/IE99/00069, filed on Jul. 21, 1999.

(30) Foreign Application Priority Data

| Jul. 21, 1998 | (IE) | S980594 |
| Jul. 21, 1998 | (IE) | S980595 |
| Jul. 21, 1998 | (IE) | S980596 |
| Jul. 21, 1998 | (IE) | S980597 |
| Jul. 21, 1998 | (IE) | S980598 |
| Jul. 21, 1998 | (IE) | S980599 |

(51) Int. Cl.$^7$ ................................ A61K 38/16
(52) U.S. Cl. ................... 514/8; 514/25; 424/489; 424/493; 424/494
(58) Field of Search ................ 514/8, 25, 47; 424/185.1, 489

(56) References Cited

U.S. PATENT DOCUMENTS

| 4,971,079 A | 11/1990 | Talapin et al. ............. 131/359 |
| 6,372,718 B2 * | 4/2002 | Santar et al. .............. 514/25 |
| 6,596,791 B2 * | 7/2003 | Santar et al. .............. 524/47 |

FOREIGN PATENT DOCUMENTS

WO    WO98/00180    1/1998

OTHER PUBLICATIONS

Domszy et al, Chitin Nat. Technol., "Ionic interactions between chitosan and oxidised cellulose", pp. 331–336, 1985–1986.
Chemical Abstracts, vol. 106, No. 26, "Hemostatic hemorrhoidal suppositories", Abstract No. 219613, Jun. 29, 1987.
Chemical Abstracts, vol. 125, No. 17, "Antitumor activity of hydroxythiamine . . .", Abstract No. 211981, Oct. 21, 1996.
Chemical Abstracts, vol. 106, No. 26, "Pharmaceuticals containing.alpha.–amino . . .", Abstract No. 219612, Jun. 29, 1987.
Chemical Abstracts, vol. 110, No. 14, "Production of oxidized cellulose–based sorbent . . .", Abstract No. 121463, Apr. 3, 1989.
Michaeli et al, SCIENCE, vol. 166, "Localization of Antigen Determinants in the Polypeptide . . .", pp. 1522–1524, 1969.

* cited by examiner

*Primary Examiner*—Robert A. Wax
*Assistant Examiner*—Anand Desai
(74) *Attorney, Agent, or Firm*—Jacobson Holman PLLC

(57) ABSTRACT

A slow release formulation includes a biocompatible anionic polysaccharide material containing glucuronic acid in the polymer chain.

38 Claims, No Drawings

SLOW RELEASE FORMULATIONS COMPRISING ANIONIC POLYSACCHARIDE

CROSS REFERENCE TO RELATED APPLICATION

This application is a continuation application claiming the benefit of priority from the prior application PCT/IE99/00069, filed Jul. 21, 1999.

INTRODUCTION

The invention relates to slow release formulations.

One of the most important parameters defining the effect of a drug applied to the organism is its physicochemical characteristics. Properties underlying the application of the drug may be acquired during its synthesis or else in the particular dosage form only.

Aside from topically applied drugs, most drugs are delivered through what may be called a "water path" within the organism. Most organic drugs, on the other hand, are also soluble in hydrophobic media such as lipids. A related characterisitic is the distribution coefficient defined as the ratio of solubility in non-polar (lipids) and polar (water) media. It's value affects not only the delivery rate of the drug to the target site in the organism, but also the duration of it's effect.

The best known and simplest method of affecting both the delivery rate and the duration of effect of an active substance in the organism is the creation of it's salt using a suitable salt-forming ion. So called Hosmeister lyotropic ion series have been established to classify the ions according to the size of their hydration/solvation envelopes which determines the solubility of the salts in a particular environment.

The most important indifferent cation and anion, not contributing to the physiological properties of a drug, are $Na^+$ and CI ions. Interesting salt-forming, though physiologically not fully indifferent anions are carboxylate anions such as those derived from citric, lactic, tartaric, glycolic, gluconic, or glucuronic acids.

Drug salts containing these anions are generally less soluble than chlorides or sulphates and therefore tend to display a prolonged or protracted effect of the drug.

Prolongation of the effect of the active substance of a drug can be attained through the use of a similar salt of the substance having a limited solubility.

Prolongation can also be achieved by fixing the active substance to ionogenic functional groups of a suitable type of polymer.

This invention is directed towards providing a polymer system to achieve slow release of an active drug in the organism.

The invention in particular involves the use of polyanhydroglucuronic acids and salts thereof. The term polyanhydroglucuronic acid and salts there of as used herein also includes copolymers thereof, especially with anhydroglucose. This is hereinafter referred to as PAGA.

Co-pending patent application PCT IE98/00004 describes particular polyanhydroglucuronic acids and salts thereof and a method of preparing such compounds. In particular therefore, the term polyanhydroglucuronic acids and salts thereof includes the acids and salts referred to in this co-pending application.

STATEMENTS OF INVENTION

We have now found that fixation of suitable types of drugs to microdispersed or microfibrillar PAGA, and salts, complex salts, or intermolecular polymer complexes thereof, preferably as prepared according to the method disclosed in PCT IE/98/00004, can be used as a means for preparing drug dosage forms with a significantly protracted effect and a reduced toxicity.

A prolongation of the effect of a drug fixed to this type of polymer chain makes it possible to reduce the amounts dosed and the frequency of dosing and thereby makes the therapy more comfortable for the patient and reduces potential systemic toxicity of the drug, the latter issue being especially of concern with, for instance, certain types of antibiotics or cytostatics.

When the polymer matrix is biodegradable. The matrix, insoluble at the origin, can then be degraded by hydrolysis or an enzyme-assisted hydrolysis in the organism whereby it slowly releases the active substance fixed to the ionogenic groups of the structural units of the biopolymer and makes it free to permeate through biological membranes.

We have found that microdispersed and microfibrillar PAGA, containing uronic carboxyl groups in the polysaccharidic polymer chain, owing to it's small particle size, high porosity and high specific surface area, and a fully open inner surface, appears to be an ideal biopolymer suitable for physicochemical fixation of a number of biologically active substances.

The open inner surface makes it possible for the molecules of the active substance to uniformly penetrate into the polymer matrix and to get uniformly fixed thereto by way of formation of either a simply salt of an acetate type or a complex salt. This uniformity, in turn, provides for a uniform release of the active substance and for the uniformity of it's effect in the organism.

Though an appropriate selection of the amount of the active substance, selection of further cations fixed to the polysaccharidic polymer chain, and possibly introduction of a certain density of cross links within the chain, it is possible to influence and vary the rate of the release from the polymer matrix. A pronounced prolongation of the drug effect and reduction of systemic toxicity with, for example, cytostatic drugs can be achieved, and the release of the active substance from the matrix can be well controlled.

Last but not least, a concomittant contribution to the reduction of drug toxicity can be attained owning to the release of glucuronic acid, which is a detoxication agent of a mammalian organism, simultaneously occurring during the biodegradation of the polymer matrix.

According to the invention there is provided a slow release formulation including a biocompatible anionic polysaccharide material containing glucuronic acid in the polymer chain.

Preferably at least 5% of the basic structural units are glucuronic acid.

Preferably the polysaccharide material is polyanhydroglucuronic acid, biocompatible salts thereof, copolymers thereof, or a biocompatible intermolecular complex thereof.

In a preferred embodiment of the invention the biocompatible intermolecular polymer complex is a complex of:
an anionic component comprising a linear or branched polysaccharide chain containing glucuronic acid; and
a non protein cationic component comprising a linear or branched natural, semi-synthetic or synthetic oligomer or polymer.

Preferably at least 5% of the basic structural units of the anionic component are glucuronic acid.

The cationic component preferably contains nitrogen that either carries a positive charge or wherein the positive charge is induced by contact with the polysaccharidic anionic component.

The cationic component may be selected from derivatives of acrylamide, methacrylamide and copolymers thereof. In this case the cationic component is selected from polyacrylamide, copolymer of hydroxyethylmethacrylate and hydroxypropylmetacrylamide, copolymers of acrylamide, butylacrylate, maleinanhydride and/or methylmetacrylate.

In one embodiment the cationic component is a cationised natural polysaccharide.

Preferably the polysaccharide is a starch, cellulose or gum.

The gum is preferably guargumhydroxypropyltriammonium chloride.

Alternatively the cationic component is a synthetic or semi-synthetic polyamino acid. In this case preferably the cationic component is polylysin, polyarginin, or $\alpha,\beta$-poly-[N-(2-hydroxyethyl)-DL-aspartamide].

In another embodiment the cationic component is a synthetic anti-fibrinolytic.

In this case preferably the anti-fibrinolytic is a hexadimethrindibromide (polybren).

Alternatively the cationic component is a natural or semi-synthetic peptide.

In this case preferably the peptide is a protamine, gelatine, fibrinopeptide, or derivatives thereof.

In another embodiment the cationic component is an aminoglucane or derivatives thereof.

In this case preferably the aminoglucane is fractionated chitin or its de-acetylated derivative chitosan. The aminoglucane may be of microbial origin or is isolated from the shells of arthropods such as crabs.

In an especially prepared embodiment of the invention the anionic component is polyanhydroglucuronic acid and/or biocompatible salts and/or copolymers thereof.

Most preferably the polyanhydroglucuronic acid and salts thereof contain in their polymeric chain from 8 to 30 percent by weight of carboxyl groups, at least 80 percent by weight of these groups being of the uronic type, at most 5 percent by weight of carbonyl groups, and at most 0.5 percent by weight of bound nitrogen.

Preferably the polyanhydroglucuronic acid and salts thereof contain in their polymeric chain at most 0.2 percent by weight of bound nitrogen.

In a preferred embodiment the molecular mass of the polymeric chain of the anionic component is from $1 \times 10^3$ to $3 \times 10^5$ Daltons.

Most preferably the molecular mass of the polymeric chain of the anionic component ranges from $5 \times 10^3$ to $1.5 \times 10^5$ Daltons.

In one embodiment of the invention the content of carboxyl groups is in the range of from 12 to 26 percent by weight, at least 95 percent of these groups being of the uronic type.

Preferably the anionic component contains at most 1 percent by weight of carbonyl groups.

In a preferred embodiment the carbonyl groups are intra- and intermolecular 2,6 and 3,6 hemiacetals, 2,4-hemialdals and C2–C3 aldehydes.

In a preferred embodiment the cationic component is gelatine.

In another preferred embodiment the cationic component is chitosan.

The composition may include at least one biocompatible biologically active substance.

Alternatively or additionally the composition includes at least one biologically acceptable adjuvant.

The composition may include at least one pharmaceutically active adjuvant.

In this case the adjuvant may be an anti-ulcer agent such as an antibiotic which is active against Helicobacter pylori e.g. clarithyromycin and/or a $H_2$-antagonist e.g. cimetidine.

The composition may also include bismuth salt.

The composition is preferably in a form for oral administration.

The composition may be in the form of a tablet, pellet, capsule, granule, or microsphere.

We have now found that by preparing polymeric intermolecular complexes (IMC) of glucuronoglucanes, notably microdispersed PAGA, prepared especially according to PCT IE 98/00004 it is possible to enhance the haemostatic effect of the final products on this basis and the properties of the temporary wound cover formed after the haemostasis is achieved such as its flexibility and resistance to cracking on movable parts of the body.

It is also possible to upgrade physicomechanical properties of the final products on this basis. Such IMCs make it possible to prepare application forms whose manufacture from a pure PAGA or their simple salts is extremely difficult. Such application forms includes non-woven textile-like structures or polymeric films. To modify or upgrade the physical mechanical properties it is sufficient to use even a relatively small amount of polymeric counterion while it is possible to obtain suitable application properties within a broad concentration range of the components. The ratio of the glucuronoglucane to polymeric counterion can be 0.99:0.01 to 0.01:0.99.

Another advantage of glucuronoglucane based IMCs is the possibility to control their biological properties such as varying the degree of haemostatis, resorption time, or immunomodulative properties, and the like.

Polymeric cations suitable to form IMCs with glucuronoglucanes prepared for example according to PCT IE 98/00004 may roughly be subdivided to the following groups:

1. Synthetic biocompatible nitrogen-containing oligomers and polymers.
   a) Derivatives of acrylamide and methacrylamide and their copolymers [such as polyacrylamide, copolymer of hydroxyethylmetacrylate and hydroxypropylmetacrylamide, copolymer of acrylamide, butylacrylate, maleinanhydride, and methylmetacrylate, and the like], or else cationised natural polysaccharides such as starches, celluloses, or gums such as guargumhydroxypropyltriammonium chloride.
   b) Synthetic or semi-synthetic polyaminoacids such as polylysin, polyarginin, $\alpha,\beta$-poly-[N-(2-hydroxyethyl)-DL-asparamide. Synthetic antifibrinolytics hexadimethrindibromide (polybren) can also be included in this group.
2. Natural or semi-synthetic peptides such as gelatine, protamines, or fibrinopeptides, and their derivatives.
3. Natural aminoglucanes such as fractionated chitin and its de-acetylated derivative chitosan, of microbial origin or isolated from the shells of arthropods such as crabs.

In preparing IMCs on the basis of PAGA according to the invention these three groups of substances can be combined to obtain required properties of the final product.

In general it can be said that IMCs using substances from 1a and 1b would preferably be used to prepare various types of highly absorbant biocompatible dressing materials in the form of nonwovens, films, plasters, and pads.

IMCs using the substances from 2 and 3 may serve as efficient haemostatic agents for internal applications in the microfibrillar form, in the microdispersed form as dusting powders, in the form of films, granules, tablets or non-woven textile-like structures. Those preparations also display antiadhesive properties.

We have also found out that in the form of film-like cell culture matrices the latter IMCs incorporating PAGA and salts thereof as prepared according to PCT IE 98/00004 have a favourable effect on the growth of fibroblasts and keratinocytes.

While it is also possible to create IMCs using structural scleroproteins of the collagen type as disclosed in WO 9800180A, it is preferable to use the above mentioned groups of substances because of the possibility of contamination of the final product by telopeptides, viruses or pyrogens. Collagen can affect in an uncontrolled manner, the immune response of the organism because formation of antibodies can be provoked by any portion of the collagen structure even though the main determinants occur in the terminal regions of the collagen macromolecule. Removal of telopeptides only partially solves the antigenicity problem (Michaeli et al: Science, 1969, 166, 1522).

By preparing IMCs according to the invention it is possible to essentially enhance properties of the originally prepared glucoronoglucanes such as 1,4 β PAGA. For instance an intermolecular complex salt of PAGA and gelatine in one single production step can be used to prepare final products in the form of a non woven, film, microdispersed granules, or dispersions. In contrast to collagen, suitably hydrolysed gelatine is well tolerated, has no toxicity or side effects and it is a much less costly raw material. We have found out that this complex has very good haemostatic properties being about 40% higher than the original PAGA calcium sodium salt. This is despite the fact that the gelatine itself only displays a haemostatic effect after an addition of thrombin [Schwartz S. I. et al.: Principles of Surgery, St.Louis: McGraw Hill Co, 1979, p. 122–123]. In this case the absorption in the organism can be controlled by changing the composition of the complex within the range from tens of hours to several months. With an advantage this complex with a higher haemostatic efficiency can be used as an embolisation or microembolisation product. It can also be used to prepare haemostatic layers of highly absorbent multi-layer dressings or resorbable plasters, though more costly polybren or protamines could also be applied.

An important advantage of these IMCs is the fact that the compounds can be prepared within a single manufacturing operation using the hydrolytic process described in PCT IE 98/00004 which makes these products cost effective.

These IMCs can further be modified by biologically active and/or biologically acceptable substances. Because the IMCs prepared by the present procedure are either of a microdispersed or microfibrillar nature, the active substances tend to be bound uniformly and also are uniformly released in the organism without the need for other adjuvants such as micrcrystalline waxes or stearates. However, the addition of such adjuvants is not excluded.

Biologically active substances which can be incorporated into the IMC may involve, for instance, antibiotics carrying at least a weak positive charge in the molecule such as cephalosporins (cephotaxin), aminoglycosides (neomycin, gentamycin, amikacin), penicillins (tikarcilin) or macrolides (erythromycin, clarithromycin) and the like.

In cases where the calcium/sodium salt of PAGA or its IMC complexes according to the invention are used as microembolisation or embolisation agents in regional chemotherapy of malign tumours, suitable types of cytostatics such as adriamycin or derivatives of 1,4-diaminoanthrachinone can be incorporated. It is also possible to use the IMCs as detaching ligands for platinum(II) based cytostatics.

Biologically acceptable substances used for modification of the IMCs include, for instance, glycerol and its polymers (polyglycerols); mono, di, and certain triglycerides; polyethyleneglycols; monopropyleneglycol; block copolymers of polyethyleneoxides and polypropyleneoxides (Pluronic); starches; cyclodextrines; polyvinylalcohols; cellulose and its derivatives; in general, substances that, in the concentrations used, are not irritating or toxic for the living organism while being capable of further optimising the physicomechanical properties of the final product based on the IMCs according to the invention.

DETAILED DESCRIPTION

The invention will be more clearly understood from the following description thereof given by way of example only.

EXAMPLES OF POLYMER COMPLEXES OF GLUCURONOGLUCANES

EXAMPLE 1

Material long-fibre cotton—medicinal cotton wool oxidised by $N_xO_y$ (proprietary)

| | |
|---|---|
| $C_6OOH$ | 18.8% b/w |
| ash content | <0.1% b/w |
| Σ C=O | 0.6% b/w |

20% solution $Na_2CO_3$ (Lachema, a.s. Neratovice)
$CaCl_2.6H_2O$ anal.grade (Lachema, a.s. Neratovice)
demineralised water 2 μS
ethanol, synthetic rectified conc. 98% (Chemopetrol Litvinov, a.s.)
acid acetic anal.grade (Lachema, a.s. Neratovice)
$H_2O_2$ anal.grade 30% (Lachema, a.s. Neratovice)
N-HANCE 3000 guargumhydroxypropyltriammoniumchloride (Aqualon-Hercules)

Equipment mixer: bottom stirring, 150 l (duplicator), stainless steel EXTRA S
vibrating screen: stainless steel, 150 mesh
rotary air pump: rotor diameter 150 mm
turbostirrer: ULTRA TURAX (Janke-Kunkel)
beaker: 5 l
pH meter PICCOLO
thermocouple thermometer Procedure 30 g of N-HANCE 3000 were placed into and 5 l beaker and 3 l of demineralised water 2 μS were added. Contents of the beaker were intensely stirred for 30 minutes. The pH value was adjusted to less than 4.5 by addition of an acetic acid solution leading to a viscosity rise.

60 l of demineralised water 2 μS were introduced into a mixer. Then 3 kg of $CaCl_2.6H_2O$ anal.grade were added and the contents heated up to a temperature of 50° C. under stirring. On dissolution of the calcium chloride the stirring was interrupted and 2.7 kg of the raw oxidised cotton wool were introduced. The mixer was closed and the contents were agitated for 120 seconds. Then the pH value of the contents was adjusted by addition of a 20% solution of $Na_2CO_3$ to 6–6.5 and 13 kg of $H_2O_2$ 30% were introduced. The fibre suspension was slowly agitated for 10 minutes. Then the pH value was readjusted to 4.5–5.0 and the prepared viscous solution of N-HANCE 3000 was introduced. The contents of the mixer were stirred intensely for 30 seconds. Subsequently 60 l of synthetic rectified ethanol conc. 98% were introduced into the mixer. After another 15 seconds from adding the ethanol the contents of the mixer were transferred onto a vibrating screen, and the supernatant. Liquid was filtered off. The filtration cake was redispersed in the mixer in 60 l of a mixture of 18 l of synthetic rectified ethanol conc. 98% and 42 l of demineralised water 2 $\mu$S. The fibre suspension was filtered again on the vibrating screen.

The isolated material thus prepared may further serve to prepare final products of the nonwoven type via a wet or dry process.

| Analysis: | |
|---|---|
| Ca content | 4.0% b/w |
| Na content | 1.8% b/w |
| Σ C=O content | 0.0% b/w |
| COOH content | 20.7% b/w |

Example 2

Material oxidised short-fibre cotton (Linters—Temming) (proprietary)

| | |
|---|---|
| $C_6OOH$ | 16.8% b/w |
| ash content | <0.15% b/w |
| Σ C=O | 2.6% b/w |

20% solution $Na_2CO_3$ (Lachema, a.s. Neratovice)
$CaCl_2.6H_2O$ anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)

Equipment turbostirrer: ULTRA TURAX (Janke-Kunkel)
sulphonation flask 1 l
heater 1.5 kW
laboratory centrifuge: 4000 rpm
thermostated water bath
pH meter PICCOLO
glass thermometer
rotary vacuum dryer or hot-air dryer Procedure Into a 1 sulphonation flask equipped with a turbostirrer and a heater, 400 ml of redistilled $H_2O$ were placed, 15.73 g of $CaCl_2.6H_2O$ were added and on dissolution, 40.0 g of 20% $Na_2CO_3$ solution were introduced under stirring. Subsequently, 50 g of oxidised Linters were added to the white emulsion formed and the contents were heated up to 95° C. and the stirring intensity set to a maximum. After 10 minutes, 30 g of 30% $H_2O_2$ were added into the flask and the hydrolysis continued for another 10 minutes. The contents were then cooled down to 60° C. on a water bath and the pH of the system was adjusted to a value of 4.5–5.0 by addition of 20% solution of $Na_2CO_3$. Furthermore, gelatine solution (10 g of gelatine in 70 g of redistilled $H_2O$) warmed up to 50° C. was added and let to react for another 20 minutes. The flask contents were then cooled down to 30° C. in a water bath and 626 ml of synthetic rectified ethanol conc. 98% were added gradually under intense stirring. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

| Analysis: | |
|---|---|
| content Ca | 4.4% b/w |
| content Na | 2.7% b/w |
| content Σ C=O | 0.0% b/w |
| content COOH | 20.5% b/w |
| content N | 1.8% b/w |

EXAMPLE 3

Material oxidised short-fibre cotton (Linters—Temming) (proprietary)

| | |
|---|---|
| $C_6OOH$ | 16.8% b/w |
| ash content | <0.15% b/w |
| Σ C=O | 2.6% b/w |

NaOH anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)

Equipment turbostirrer: ULTRA TURAX (Janke-Kunkel)
sulphonation flask 1 l
heater 1.5 kW
laboratory centrifuge: 4000 rpm
thermostated water bath
pH meter PICCOLO
glass thermometer
rotary vacuum dryer or hot-air dryer Procedure Into a 1 l sulphonation flask equipped with a turbostirrer and a heater, 400 ml of redistilled $H_2O$ were placed, and 8 g of NaOH were added. On dissolution, 50 g of oxidised Linters were added, the contents were heated up to 70° C. and the stirring intensity set to a maximum. After 20 minutes, 40 g of 30% $H_2O_2$ were added into the flask, temperature was increased to 85° C., and maintained for another 10 minutes. The contents were then cooled down to 50° C. on a water bath and gelatine solution (10 g of gelatine in 70 g of redistilled $H_2O$) warmed up to 50° C. was added to the hydrolysate. The temperature was decreased to 25–30° C. and the pH of the system was checked and adjusted to a value of 6.0–6.5. Subsequently, 626 ml of synthetic rectified ethanol conc. 98% were added gradually under intense stirring. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

| Analysis: | |
|---|---|
| Na content | 3.8% b/w |
| Σ C=O content | 0.0% b/w |
| COOH content | 22.5% b/w |
| N content | 2.7% b/w |

EXAMPLE 4

Material
  oxidised short-fibre cotton (Linters—Temming) (proprietary)

| $C_6OOH$ | 16.8% b/w |
|---|---|
| ash content | <0.15% b/w |
| Σ C=O | 2.6% b/w |

20% solution $Na_2CO_3$ (Lachema, a.s. Neratovice)
  $CaCl_2.6H_2O$ anal.grade (Lachema, a.s. Neratovice)
  redistilled water (PhBs 1997)
  ethanol, synthetic rectified conc. 98% (Chemopetrol Litvinov, a.s.)
  isopropanol 99.9% (Neuberg Bretang)
  $H_2O_2$ anal.grade 30% (Lachema, a.s. Neratovice)
  chitosan, degree of deacetylation 92% (Henkel)
Equipment
  turbostirrer: ULTRA TURAX (Janke-Kunkel)
  sulphonation flask 11
  heater 1.5 kW
  laboratory centrifuge: 4000 rpm
  thermostated water bath
  pH meter PICCOLO
  glass thermometer
  rotary vacuum dryer or hot-air dryer Procedure Into a sulphonation flask, 250 ml redistilled $H_2O$ were placed, and 5 g of NaOH were added. On dissolution, 25 g of oxidised Linters were introduced under stirring, the temperature increased to 50° C. and the stirring intensity set to a maximum. After hydrolysing for 15 minutes, 35 g of 30% $H_2O_2$ were gradually added to the system and the temperature was maintained at 50° C. for another 20 minutes. The content were cooled down to 30° C. and 400 g of highly viscous 5% solution of chitosan were added. The flask contents were then intensely stirred for another 10 minutes, and the pH of the system was adjusted, by addition of NaOH, to a value of 7.0. Subsequently 300 ml of synthetic rectified ethanol conc. 98% were added under stirring. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

| Analysis: | |
|---|---|
| Na content | 1.8% b/w |
| Σ C=O content | 0.0% b/w |
| COOH content | 10.4% b/w |
| N content | 2.8% b/w |

EXAMPLE 5

Material
  oxidised short-fibre cotton (Linters—Temming) (proprietary)

| $C_6OOH$ | 16.8% b/w |
|---|---|
| ash content | <0.15% b/w |
| Σ C=O | 2.6% b/w |

NaOH anal.grade (Lachema, a.s. Neratovice)
  HCl 39% anal.grade (Lachema, a.s. Neratovice)
  redistilled water (PhBs 1997)
  ethanol, synthetic rectified conc. 98% (Chemopetrol Litvinov, a.s.)
  isopropanol 99.9% (Neuberg Bretang)
  $H_2O_2$ anal.grade 30% (Lachema, a.s. Neratovice)
  gelatine (PhBs 1997)
  Ambroxol (H. Mack, Germany)
Equipment
  turbostirrer: ULTRA TURAX (Janke-Kunkel)
  sulphonation flask 21
  heater 1.5 kW
  laboratory centrifuge: 4000 rpm
  laboratory pin mill ALPINE (35 000 rpm)

thermostated water bath pH meter PICCOLO glass thermometer rotary vacuum dryer or hot-air dryer Procedure Into a sulphonation flask, 400 ml redistilled $H_2O$ were placed, and 8 g of NaOH were added. On dissolution, 50 g of oxidised Linters were introduced under stirring, the temperature increased to 70° C. and the stirring intensity was set to a maximum. After hydrolysing for 20 minutes, 40 g of 30% $H_2O_2$ were gradually added to the system and the temperature was increased to, and maintained at, 85° C. for another 10 minutes. The content were cooled down to 50° C. in a water bath, and gelatine solution (2 g of gelatine in 70 g of redistilled $H_2O$) warmed up to 50° C. was added to the hydrolysate. The temperature was decreased to 25–30° C. and the pH of the system was checked and adjusted to a value of 1.6–1.8 by addition of 39% HCl. Under intense stirring, a solution of Ambroxol (25 g of ambroxolium hydrochloride in 500 ml of redistilled $H_2O$) was added gradually. After agitating for 5 minutes the pH value was adjusted to 4.3–4.6 by adding 5% NaOH solution, and 626 ml of synthetic rectified ethanol conc. 98% were added under intense stirring. The suspension of Ambroxol containing IMC thus formed was isolated using a laboratory centrifuge. The supernatant liquid was filtered away and the cake was redispersed into, subsequently, 800 ml of 60% ethanol and 250 ml of 98% ethanol, wherein it was let to stay for a minimum of 10 hours. The system was centrifuged again and the product was dried at 40° C. in a rotary vacuum dryer or a hot-air dryer. A white to slightly yellowish powder was obtained and further desagglomerated on an Alpine pin mill.

The product serves for the preparation of a mucoregulatory drug with a prolonged action.

| Analysis: | |
| --- | --- |
| Na content | 4.6% b/w |
| Σ C=O content | 0.0% b/w |
| COOH content | 14.8% b/w |
| N content | 1.9% b/w |

EXAMPLE 6

Material oxidised short-fibre cotton (Linters—Temming) (proprietary)

| | |
| --- | --- |
| $C_6OOH$ | 16.8% b/w |
| ash content | <0.15% b/w |
| Σ C=O | 2.6% b/w |

20% solution $Na_2CO_3$ (Lachema, a.s. Neratovice)

$CaCl_2.6H_2O$ anal.grade (Lachema, a.s. Neratovice)

redistilled water (PhBs 1997)

ethanol, synthetic rectified conc. 98% (Chemopetrol Litvinov, a.s.)

isopropanol 99.9% (Neuberg Bretang)

$H_2O_2$ anal.grade 30% (Lachema, a.s. Neratovice)

gelatine (PhBs 1997)

gentamycin sulphate (MERCK)

Equipment turbostirrer: ULTRA TURAX (Janke-Kunkel)

sulphonation flask 2 l heater 1.5 kW laboratory centrifuge: 4000 rpm laboratory pin mill ALPINE (35 000 rpm)

thermostated water bath pH meter PICCOLO glass thermometer hot-air dryer lyophiliser (Leibold Heraus, Germany)

Procedure

Into a 2 l sulphonation flask equipped with a turbostirrer and a heater, 400 ml of redistilled $H_2O$ were placed, 15.73 g of $CaCl_2.6H_2O$ were added and on dissolution, 40.0 g of 20% $Na_2CO_3$ solution were introduced under stirring. Subsequently, 50 g of oxidised Linters were added to the white emulsion formed and the contents were heated up to 95° C. and the stirring intensity set to a maximum. After 10 minutes, 30 g of 30% $H_2O_2$ were added into the flask and the hydrolysis was continued for another 10 minutes. The contents were then cooled down to 60° C. on a water bath and the pH of the system was adjusted to a value of 4.5–5.0 by addition of 20% solution of $Na_2CO_3$. Furthermore, gelatine solution (10 g of gelatine in 70 g of redistilled $H_2O$) warmed up to 50° C. was added and let to react for another 20 minutes. The flask contents were then cooled down to 30° C. in a water bath and 40 g of gentamycin sulphate in 600 ml of redistilled $H_2O$ were added gradually within 10 minutes. 626 ml of synthetic rectified ethanol conc. 98% were then added gradually under intense stirring to the antibiotic containing IMC suspension formed. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, for the manufacture of a dusting powder or a powder spray for the treatment of infected wounds.

| Analysis: | |
| --- | --- |
| Ca content | 2.4% b/w |
| Na content | 1.6% b/w |
| Σ C=O content | 0.0% b/w |
| COOH content | 9.6% b/w |
| N content | 2.7% b/w |

EXAMPLE 7

Material long-fibre cotton—medicinal cotton wool oxidised by $N_xO_y$ (proprietary)

| | |
| --- | --- |
| $C_6OOH$ | 18.8% b/w |
| ash content | <0.1% b/w |
| Σ C=O | 0.6% b/w |

20% solution $Na_2CO_3$ (Lachema, a.s. Neratovice)

$CaCl_2.6H_2O$ anal.grade (Lachema, a.s. Neratovice)

demineralised water 2 μS
ethanol, synthetic rectified conc. 98% (Chemopetrol Litvinov, a.s.)
isopropanol 99.9% (Neuberg Bretang)
acid acetic anal.grade (Lachema, a.s. Neratovice)
H$_2$O$_2$ anal.grade 30% (Lachema, a.s. Neratovice)
N-HANCE 3000 guargumhydroxypropyltriammoniumchloride
(Aqualon-Hercules)
polybren (hexadimethrindibromide) (FLUKA)
chlorhexidindigluconate Equipment
mixer: bottom stirring, 150 l (duplicator), stainless steel EXTRA S
vibrating screen: stainless steel, 150 mesh
rotary air pump: rotor diameter 150 mm
turbostirrer: ULTRA TURAX (Janke-Kunkel)
beaker: 5 l
pH meter PICCOLO
thermocouple thermometer Procedure
30 g of N-HANCE 3000 were placed into and 5 l beaker and 3 l of demineralised water 2 μS were added. Contents of the beaker were intensely stirred for 30 minutes. The pH value was adjusted to less than 4.5 by addition of an acetic acid solution leading to a viscosity rise.

60 l of demineralised water 2 μS were introduced into a mixer. Then 3 kg of CaCl$_2$.6H$_2$O anal.grade were added and the contents heated up to a temperature of 50° C. under stirring. On dissolution of the calcium chloride the stirring was interrupted and 2.7 kg of the raw oxidised cotton wool were introduced. The mixer was closed and the contents were agitated for 120 seconds. Then the pH value of the contents was adjusted by addition of a 20% solution of Na$_2$CO$_3$ to 6–6.5 and 13 kg of H$_2$O$_2$ 30% were introduced. The fibre suspension was slowly agitated for 10 minutes. Then the pH value was readjusted to 4.5–5.0 and the prepared viscous solution of N-HANCE 3000 was introduced. The contents of the mixer were stirred intensely for 30 seconds. A solution of 35 g of chlorhexidine digluconate in 350 ml of demineralised water 2 μS was then introduced slowly within 10 minutes. Within another 10 minutes, a solution of polybren containing 120 g of polybrenu in 1000 ml of demineralised water 2 μS was added. Subsequently 60 l of synthetic rectified ethanol conc. 98% were introduced into the mixer. After another 15 seconds from adding the ethanol, the contents of the mixer were transferred onto a vibrating screen, and the supernatant. Liquid was filtered off. The filtration cake was redispersed in the mixer in 60 l of a mixture of 18 l of synthetic rectified ethanol conc. 98% and 42 l of demineralised water 2 μS. The fibre suspension was filtered again on the vibrating screen.

The isolated material thus prepared may further serve to prepare, via a wet or dry process, final products of the nonwoven type having an enhanced haemostatic activity and a bactericidal effect.

| Analysis: | |
|---|---|
| Ca content | 3.6% b/w |
| Na content | 1.9% b/w |
| Σ C=O content | 0.0% b/w |

| -continued | |
|---|---|
| Analysis: | |
| COOH content | 18.1% b/w |
| N content | 0.35% b/w |

EXAMPLE 8

Material
oxidised short-fibre cotton (Linters—Temming) (proprietary)

| | |
|---|---|
| C$_6$OOH | 16.8% b/w |
| ash content | <0.15% b/w |
| Σ C=O | 2.6% b/w |

20% solution Na$_2$CO$_3$ (Lachema, a.s. Neratovice)
CaCl$_2$.6H$_2$O anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
H$_2$O$_2$ anal.grade 30% (Lachema, a.s. Neratovice)
Chitosan, degree of deacetylation 92% (Henkel)
Clarithromycin lactobionan (Abbott Laboratories, Italy)

Equipment:
turbostirrer: ULTRA TURAX (Janke-Kunkel)
sulphonation flask 1 l
heater 1.5 kW
laboratory centrifuge: 4000 rpm
thermostated water bath
pH meter PICCOLO
glass thermometer
rotary vacuum dryer or hot-air dryer
dialysing bag (regenerated cellulose)
lyophiliser (Leybold Heraus, Germany)
laboratory pin mill ALPINE (35 000 rpm)

Procedure
Into a sulphonation flask, 250 ml redistilled H$_2$O were placed, and 5 g of NaOH were added. On dissolution, 25 g of oxidised Linters were introduced under stirring, the temperature increased to 50° C. and the stirring intensity set to a maximum. After hydrolysing for 15 minutes, 35 g of 30% H$_2$O$_2$ were gradually added to the system and the temperature was maintained at 50° C. for another 20 minutes. The content were cooled down to 30° C. and 400 g of highly viscous 2% solution of chitosan, having a pH value of 3.5, were added. The flask contents were then intensely stirred for another 10 minutes, and the pH of the system was adjusted, by addition of NaOH, to a value of 7.0. During another 10 minutes, a solution of clarithromycin (44 g of clarithromycin in 456 ml of redistilled H$_2$O) was introduced and the pH of the system was adjusted to a value of 7.0–7.5. Stirring was interrupted, the flask contents were transferred into a dialysing bag and dialysed against water for 48 hours. Subsequently the product was isolated by centrifugation, lyophilised, and disintegrated on the laboratory pin mill ALPINE.

The product can be used, for instance, to prepare tablets or granules efficient against Helicobacter pylori occurring in the gastrointestinal tract.

| Analysis: | |
|---|---|
| Na content | 4.8% b/w |
| Σ C=O content | 0.0% b/w |
| COOH content | 18.8% b/w |
| N content | 0.7% b/w |

EXAMPLE 9

Material
   oxidised short-fibre cotton (Linters—Temming) (proprietary)

| | |
|---|---|
| $C_6$OOH | 16.8% b/w |
| ash content | <0.15% b/w |
| Σ C=O | 2.6% b/w |

NaOH anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)
$Bi(NO_3).5H_2O$ (MERCK)

Equipment
   turbostirrer: ULTRA TURAX (Janke-Kunkel)
   sulphonation flask 21
   heater 1.5 kW
   laboratory centrifuge: 4000 rpm
   thermostated water bath
   pH meter PICCOLO
   glass thermometer
   rotary vacuum dryer or hot-air dryer Procedure Into a sulphonation flask, 400 ml redistilled $H_2O$ were placed, and 8 g of NaOH were added. On dissolution, 50 g of oxidised Linters were introduced under stirring, the temperature increased to 70° C. and the stirring intensity was set to a maximum. After hydrolysing for 20 minutes, 40 g of 30% $H_2O_2$ were gradually added to the system and the temperature was increased to, and maintained at, 85° C. for another 10 minutes. The content were cooled down to 50° C. in a water bath, and gelatine solution (0.5 g of gelatine in 50 ml of redistilled $H_2O$) warmed up to 50° C. was added to the hydrolysate. The temperature was decreased to 25–30° C. and the pH of the system was checked and adjusted to a value of 1.6–1.8 by addition of 39% HCl. A freshly prepared solution of $BiNO_3$ (54 g of $BiNO_3.5H_2O$ in 746 ml of $H_2O$) was introduced and the temperature maintained for another 15 minutes. Then the temperature was decreased to 25–30° C. and the pH of the system was checked and readjusted to a value of 5.5–6.0. 626 ml of synthetic rectified ethanol conc. 98% were then added gradually under intense stirring to the formed. The $BiO^+$ containing IMC suspension thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for a minimum of 4 hours. It was then centrifuged again, redispersed into 99.9% isopropanol, and let to stay for a minimum of 10 hours at 20° C. The suspension formed was then centrifuged again and the product was dried in a rotary vacuum dryer or a hot-air dryer.

The product can be used, for instance, to prepare dusting powders for wound treatment or tablets for treatment of gastrointestinal tract malfunctions.

| Analysis: | |
|---|---|
| Na content | 1.9% b/w |
| Σ C=O content | 0.0% b/w |
| COOH content | 20.0% b/w |
| N content | <0.3% b/w |
| Bi content | 4.7% b/w |

Example 10

Material
   oxidised short-fibre cotton (Linters—Temming) (proprietary)

| | |
|---|---|
| $C_6$OOH | 16.8% b/w |
| ash content | <0.15% b/w |
| Σ C=O | 2.6% b/w |

20% solution $Na_2CO_3$ (Lachema, a.s. Neratovice)
$CaCl_2.6H_2O$ anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)
cimetidine hydrochloride (SPOFA)

Equipment
   turbostirrer: ULTRA TURAX (Janke-Kunkel)
   sulphonation flask 21
   heater 1.5 kW
   laboratory centrifuge: 4000 rpm
   thermostated water bath
   pH meter PICCOLO
   glass thermometer
   rotary vacuum dryer or hot-air dryer Procedure Into a 1 l sulphonation flask equipped with a turbostirrer and a heater, 400 ml of redistilled $H_2O$ were placed, 15.73 g of $CaCl_2.6H_2O$ were added and on dissolution, 40.0 g of 20% $Na_2CO_3$ solution were introduced under stirring. Subsequently, 50 g of oxidised Linters were added to the white emulsion formed and the contents were heated up to 95° C. and the stirring intensity set to a maximum. After 10 minutes, 30 g of 30% $H_2O_2$ were added into the flask and the hydrolysis was continued for another 10 minutes. The contents were then cooled down to 60° C. on a water bath and the pH of the system was adjusted to a value of 4.5–5.0 by addition of 20% solution of $Na_2CO_3$. Furthermore, gelatine solution (10 g of gelatine in 70 g of redistilled $H_2O$) warmed up to 50° C. was added and let to react for another 20 minutes. The flask contents were then cooled down to 30° C. in a water bath and a solution of cimetidine (36 g of cimetidine hydrochloride in 400 ml of redistilled $H_2O$) were added under intens stirring. The contents were intensely agitated for 10 minutes and 800 ml of synthetic rectified ethanol conc. 98% were then added gradually. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, to manufacture tablets or granulates for the treatment of the gastrointestinal tract or other non-malignant ulcerations.

Analysis:

| | |
|---|---|
| Ca content | 4.4% b/w |
| Na content | 2.7% b/w |
| Σ C=O content | 0.0% b/w |
| COOH content | 20.5% b/w |
| N content | 2.1% b/w |

EXAMPLE 11

Material
- IMC-MDOC complex (as per above Example 2)
- [(2S;2R)-3-amino-2-hydroxy4-phenylbutenoyl]-L-leucin (Bestatin)
- (Boehringer Mannheim, Germany)
- redistilled water (PhBs 1997)
- methanol, conc. anal.grade (Chemopetrol Litvinov, a.s.)
- diethylether (Lachema, a.s. Neratovice)

Equipment
- turbostirrer: ULTRA TURAX (Janke-Kunkel)
- sulphonation flask 21
- laboratory centrifuge: 4000 rpm
- hot-air dryer Procedure The IMC-MDOC complex as prepared in Example 2 above was redispersed into redistilled water in a sulphonation flask using a turbostirrer. A solution of Bestatin in methanol was then added to the flask in an amount sufficient to yield a 10% b/w concentration of Bestatin in the resulting Bestatin-gelatine-MDOC complex. After thorough homogenisation, the suspension formed was isolated by centrifugation. The supernatant liquid ws filtered away and the filtration cake was redispersed into concentrated methanol again, centrifuged, redispersed in diethylether, and after being allowed to stay for 1 hour, it was dried in a hot-air dryer.

The product, a microdispersed form of a Bestatin-gelatine-MDOC complex, can be used, for instance, to prepare microembolisation agents used in regional chemotherapy of malignant tumours or flat dressing structures for wound treatment.

EXAMPLE A

Preparation of Tablets and Pellets With IMC-MDOC Complex Containing Clarithromycin MDOC=Microdispersed Oxidised cellulose Material
- IMC-MDOC complex—see Example 8
- MDOC, particle size 0.1–2.0 μm, specific surface area 86 m², COOH group content 22.2% b/w, Ca content 4.2% b/w, Na content 3.8% b/w
- IMC-MDOC complex containing $BiO^+$—see Example 9

Equipment
- laboratory mixer, bottom agitated, 4000 rpm tabletting machine (KORSCH EK 0, Berlin)

Procedure 9.5 g of IMC-MDOC containing clarithromycin were placed into the mixer, and 12.0 g of $BiO^+$ salt and 78.5 g of MDOC were added. The vessel was closed, the agitation begun, and the contents homogenised for 60 seconds. The homogenised mixture was then transferred to the storage vessel of the tabletting machine. The tabletting force was set to a value of 7.5 kN.

Result

The tablets prepared were smooth and cohesive and had a weight of 0.5 g. Disintegration rate of the tablets in a saline F1/1 was 12 minutes at 20° C., and 5 minutes at 37° C.

Indication

The tablets are indicated for treatment of gastric ulcers. MDOC suppresses formation of the stomach acidity, adjusts the pH value of the environment, and protects the mucous membranes by forming a gel layer. $BiO^+$ acts as a mild astringens. Clarithromycin depresses the growth of Helicobacter pylori beyond pathologic limits.

EXAMPLE B

Preparation of Tablets and Pellets With IMC-MDOC Complex Containing Ambroxol

Material
- MDOC, particle size 0.1–2.0 μm, specific surface area 86 m², COOH group content 22.2% b/w, Ca content 4.2% b/w, Na content 3.8% b/w
- IMC-MDOC complex containing Ambroxol—see Example 5
- microcrystalline cellulose (SIGMA)
- hydroxypropylcellulose (Natrosol HHR 250)
- magnesium stearate (SIGMA)
- Macrogol 400 (SIGMA)

Equipment
- laboratory mixer, bottom agitated, 4000 rpm tabletting machine (KORSCH EK 0, Berlin)

Procedure 43.0 g MDOC, 42.0 g IMC-MDOC containing ambroxol, 10.0 g microcrystalline cellulose, 2.0 g magnesium stearate, 1.0 g Macrogol 400 and 2.0 g Natrosol HHR 250 were introduced into the mixer. The vessel was closed, agitation at 4000 rpm begun and the contents homogenised for 120 seconds. The homogenised mixture was then transferred to the storage vessel of the tabletting machine. The tabletting force was set at a value of 5.0 kN.

Result

The tablets prepared were smooth and cohesive and had a weight of 0.5 g. Disintegration rate of the tablets in a saline F1/1 was 10 minutes at 20° C., and 6 minutes at 37° C.

Indication

Acute and chronic respiratory diseases involving formation of dense mucus (acute bronchitus, bronchial asthma), ease of mucus dissolution in rhinofaryngitis. In testing on volunteers at a dosage rate of 3 tablets per day, ambroxol could still be detected in the urine at Day 8 after administration.

EXAMPLE C

Preparation of Tablets and Pellets With IMC-MDOC Complex Containing Cimetidine

Material
- MDOC, particle size 0.1–2.0 μm, specific surface area 86 m², COOH group content 22.2% b/w, Ca content 4.2% b/w, Na content 3.8% b/w
- IMC-MDOC complex containing cimetidine—see Example 10 Macrogol 400 (SIGMA)

Equipment
  laboratory mixer, bottom agitated, 4000 rpm
  tabletting machine (KORSCH EK 0, Berlin)
Procedure
  63.0 g IMC-MDOC containing cimetidine, 32.0 g MDOC and 5.0 g Macrogol 400 were introduced into the mixer. The vessel was closed, agitation begun, and the contents were homogenised for 60 seconds. The homogenised mixture was then transferred to the storage vessel of the tabletting machine. The tabletting force was set to a value of 7.5 kN.
Result
  The tablets prepared were smooth and cohesive and had a weight of 1.0 g. Disintegration rate of the tablets in a saline F1/1 was 8 minutes at 20° C., and 6 minutes at 37° C.
Indication
  The tablets are indicated for treatment of gastric ulcers. MDOC suppresses formation of the stomach acidity, adjust the pH value of the environment, and protects the mucous membranes by forming a gel layer. $BiO^+$ acts as a mild astringens. Cimetidine suppresses both basal and simulated secretion of the stomach acid.

EXAMPLE D

Preparation of Rectal Suppositories From IMC-MDOC $BiO^+$ Complex Containing Aminophenazon and Allobarbital Material
  Adeps neutralis (WERBA)
  Oleum cacao (WERBA)
  IMC-MDOC complex containing $BiO^+$—see Example 9
  Aminophenazonum (SPOFA)
  Allobarbitalum (SPOFA)
Equipment
  stainless melting tank, agitated, volume 1000 ml, input power 600 W movable support carrying a shaped blister foil
Procedure
  282.6 g of Adeps neutralis and 122.6 g of Oleum cacao were introduced into the melting tank. The contents were heated to a temperature of 75° C. On melting, 16 g Allobarbitalum, 117.3 g Aminophenozonum and 61.33 g IMC-MDOC complex containing $BiO^+$ were gradually added under continuous agitation. After appropriate homogenisation, the mass was cast into a shaped blister foil which serves, when cooled down, as the suppository packaging.
Result
  Suppository of 8 mm diameter, 20 mm length, conical shape, weight 2.25 g.
Indication
  Combined suppositories having antihaemorroidal and analgetic/antipyretic effects.

EXAMPLE E

Preparation of Vaginal Suppositories From IMC-MDOC Complex Containing Gelatine, Nitrofurantoin and Chlorohexidine Material
  IMC-MDOC complex—see Example 2
  gelatina animalis (SIGMA)
  1,2-monopropylenglykol (SIGMA)
  glycerol, medicinal (MERCK)
  nitrofurantoinum (SPOFA)
  chlorohexidine digluconate (FEROSAN)
  redistilled $H_2O$
Equipment
  stainless melting tank, agitated, volume 1000 ml, input power 600 W movable support carrying a shaped blister foil
Procedure
  78 g redistilled $H_2O$, 240 g medicinal glycerol, and 30 g 1,2-MPG were introduced into the melting tank and the mixture was heated to a temperature of 75° C. On melting, 30 g of nitrofurantoinum and 30 g of chlorohexidine were gradually added under agitation. The mixture was agitated for a further 15 minutes. Subsequently, 102 g of gelatine animalis were introduced and, after appropriate homogenisation, 90 g IMC-MDOC complex were added. The resulting mixture was agitated for another 15 minutes and then cast into a shaped blister foil serving, when cooled down, as the suppository packaging.
Result
  Suppository of 8 mm diameter, 17 mm length, cylindrical shape, weight 2.0 g.
Indication
  Vaginal suppositories for use in treatment of urinary tract infections due to both gram positive and gram negative bacteria, displaying a prolonged effect. The IMC-MDOC present serves to protect the vaginal mucous tissue and to create a natural microenvironment similar to the action of lactic acid.

EXAMPLE F

Preparation of Granules From IMC-MDOC Complex Containing Clarithromycin

Material
  IMC-MDOC complex—see Example 8
  MDOC, particle size 0.1–2.0 µm, specific surface area 86 $m^2/g$, COOH group content 22.2% b/w, Ca content 4.2% b/w, Na content 3.8% b/w
  IMC-MDOC complex containing $BiO^+$—see Example 9
  ethanol synthetic rectified 98%
  redistilled $H_2O$
Equipment
  set of vibrating screens with mesh size 100, 150, 200, 250, 350, 500 µm mixer, bottom agitated, vessel size 1000 ml, 8000 rpm, equipped with a nozzle for inlet of the granulation medium counter-flow drier (BINDER)
Procedure
  100 g of MDOC were placed into the mixer, the mixer was closed and the agitation begun. A mist of 88% aqueous solution of ethanol was gradually injected into the mixer at a rate of 10 g/45 seconds. The granulate formed was transferred to the counter-flow drier and dried at a temperature of 45° C. until the humidity content was reduced to below 6% b/w. The dried granules were sieve-screened using the set of vibrating screens. The individual fractions were packaged into glass vials in amounts of 0.5–2.0 g each as required. The preparation was sterilised by γ irradiation with a dose of 25 kGy.
Indication
  The granules can be used in the treatment of gastric ulcers. MDOC suppresses formation of the stomach acidity, adjusts the pH value of the environment and protects the mucous membranes by forming a gel layer. $BiO^+$ acts as a mild astringens. Clarithromycin depresses the growth of Helicobacter pylori beyond pathologic limits.

EXAMPLE G

Preparation of Microspheres From IMC-MDOC Complex Containing Mitoxanthron

Material
  IMC-MDOC complex—see Example 3
  1,4-bis-2-(-2-hydroxyethylamino-ethylamino-)5,8-dihydroxyantrachinon (mitoxanthron) (Aliachem a.s.)
  ethanol synthetic rectified 98% (Chemopetrol Litvinov, a.s.) redistilled $H_2O$ Equipment
  turbostirrer ULTRA TURAX (Janke-Kunkel)
  sulphonation flask 1 Liter
  beaker 250 ml
  set of vibrating screens with mesh size 100, 150, 200, 250, 350, 500 μm
  counter-flow drier (BINDER)
  vial 10 ml
  injection syringe 25 ml
Procedure 80 g redistilled water and 20 g IMC-MDOC complex were introduced into the beaker and the complex was dispersed using the turbostirrer to obtain a colloidal solution thereof.

495 ml 98% ethanol was placed into the sulphonation flask. 1.0 g of mitoxanthron hydrochloride was placed into the 10 ml vial and dissolved in 5 g redistilled water. The solution was then transferred into the sulphonation flask with ethanol under stirring.

The colloidal solution of IMC-MDOC complex was then gradually introduced into the mitoxantron solution by being dropped, via the injection syringe, at a rate of 20 drops per minute into the sulphonation flask. The microspheres were isolated by filtration from the supernatant liquid, cautiously redispersed into 250 ml of 98% ethanol and allowed to stand for 4 hours. The ethanol was then removed by filtration and the microspheres were dried in the counter-flow drier at a temperature of 40° C. until the humidity content was reduced to below 3% b/w. The dry microspheres containing 50 mg of mitoxanthron per 1 g were sieve-screened using the set of vibrating screens, and packaged into glass vials in amounts of 0.5 g each.

Indication

Intraarterial (regional) chemotherapy of malignant tumours where mitoxanthron is indicated.

EXAMPLE H

Preparation of Microspheres From IMC-MDOC Complex Containing Platinum(II) Compounds Material
  MDOC (Ca/Na salt of PAGA), particle size 0.1–2.0 μm, specific surface area 86 m$^2$/g, COOH group content 22.2% b/w, Ca content 4.2% b/w, Na content 3.8% b/w
  ethanol synthetic rectified 98% (Chemopetrol Litvinov, a.s.)
  redistilled H$_2$O
  1,2-dihydroxypropane (Sigma)
  polyacrylamide, 50% aqueous solution (Aldrich)
  glycerol, medicinal (PhBs 1997)
Equipment
  laboratory mixer, bottom agitated, 4000 rpm
  sulphonation flask 1 Liter
  injection syringe 25 ml
Procedure A colloidal aqueous solution of an MDOC-chitosan-polyacrylamide complex containing 30% b/w of MDOC Ca/Na salt was dropped, via the injection syringe at a rate of 10 drops per minute, into a ethanol/glycerol/water system containing salts of bivalent platinum with two ammonia (NH$_3$) ligands. The microspheres formed, contained (NH$_3$)$_2$Pt(II) groups, were isolated from the coagulating bath by decantation, washed with concentrated ethanol, and vacuum dried at 25° C.

Indication

Intraarterial (regional) chemotherapy of malignant tumours where diamoplatinum(II) complexes are indicated.

EXAMPLE I

Preparation of Rigid Foams From IMC-MDOC Complex Containing Chitosan and Bestatin Material
  IMC-MDOC bestatin complex—see Example 11
  chitosan, degree of deacetylation 92% (Henkel)
  polyacrylamide, 50% aqueous solution (Aldrich)
  glycerol, medicinal (PhBs 1997)
  redistilled H$_2$O
Equipment
  turbostirrer ULTRA TURAX (Janke-Kunkel)
  sulphonation flask 1 Liter
  laboratory heater
  counter-flow drier (BINDER)
Procedure Bestatin containing IMC-MDOC complex as prepared according to Example 11, glycerol, 25% aqueous solution of polyacrylamide, 3% solution of chitosan in acetic acid solution and redistilled water were placed into the sulphonation flask in amounts such that the glycerol content in the system attains 30% b/w and that of the IMC-MDOC complex attains 0.1% b/w. The mixture was thoroughly homogenised for 5 minutes using the turbostirrer, and n-pentane in an amount of 3%, calculated on the total volume basis, was added and dispersed into the system. The mixture was injected into suitably shaped moulds and dried to obtain flexible foamed sheets.

Indication

Suitable for use in preparation of embolisation agents, plasters and similar products.

EXAMPLE J

Preparation of Flat Textile-Like Structures Containing MDOC and IMC-MDOC Complex with Bestatin Material
  cotton dressing pad
  MDOC (Ca/Na salt of PAGA), particle size 0.1–2.0 μm, specific surface area 86 m$^2$/g, COOH group content 22.2% b/w, Ca content 4.2% b/w, Na content 3.8% b/w
  IMC-MDOC bestatin complex—see Example 11
  ethanol synthetic rectified 98% (Chemopetrol Litvinov, a.s.)
  demineralised water 2μS
Equipment
  continuous spray-coating equipment
Procedure A dispersion of MDOC Ca/Na containing 10% b/w IMC-MDOC bestatin complex prepared by the procedure according to Example 11 in 88.5% aqueous solution of ethanol was prepared within the storage tank of the spray coater. The dispersion was spray coated onto a cotton knitted pad to achieve an add-on within a range of area weights between 10 to 500 g/m$^2$. An impregnated flat textile-like structure was obtained on evaporating the aqueous ethanol.

Indication

Suitable for use in preparation of dressing materials for e.g. covering skin lesions after surgical removal of skin neoplasies.

The invention is not limited to the embodiments hereinbefore described which may be varied in detail.

What is claimed is:

1. A slow release formulation including a biocompatible anionic polysaccharide material containing glucuronic acid in a polymer chain of the polysaccharide material.

2. The formulation as claimed in claim 1 wherein at least 5% of the basic structural units of the polysaccharide are glucuronic acid.

3. The formulation as claimed in claim 1 wherein the polysaccharide material is polyanhydroglucuronic acid, biocompatible salts thereof, copolymers thereof, or a biocompatible intermolecular complex thereof.

4. The formulation as claimed in claim 3 wherein the biocompatible intermolecular polymer complex is a complex of:
   an anionic component comprising a linear or branched polysaccharide chain containing glucuronic acid; and
   a non protein cationic component comprising a linear or branched natural, semi-synthetic or synthetic oligomer or polymer.

5. The formulation as claimed in claim 4 wherein at least 5% of the basic structural units of the anionic component are glucuronic acid.

6. The formulation as claimed in claim 4 wherein the cationic component contains nitrogen that either carries a positive charge or wherein the positive charge is induced by contact with the polysaccharidic anionic component.

7. The formulation as claimed in claim 6 wherein the cationic component is selected from acrylamide derivatives, methacrylamide derivatives and copolymers thereof.

8. The formulation as claimed in claim 7 wherein the cationic component is selected from polyacrylamide, copolymer of hydroxyethylmethacrylate and hydroxypropylmetacrylamide, copolymers of acrylamide, butylacrylate, maleinanhydride and methylmetacrylate.

9. The formulation as claimed in claim 4 wherein the cationic component is a cationised natural polysaccharide.

10. The formulation as claimed in claim 9 wherein the polysaccharide is a starch, cellulose or gum.

11. The formulation as claimed in claim 10 wherein the gum is guanrgumhydroxypropyltriammonium chloride.

12. The formulation as claimed in claim 4 wherein the cationic component is a synthetic or semi-synthetic polyamino acid.

13. The formulation as claimed in claim 4 wherein the cationic component is polylysine, polyarginine, or α, β-poly-(N-(2-hydroxyethyl)-DL-aspartamide).

14. The formulation as claimed in claim 4 wherein the cationic component is a synthetic anti-fibrinolytic.

15. The formulation as claimed in claim 14 wherein the anti-fibrinolytic is a hexadimethrindibromide (polybren).

16. The formulation as claimed in claim 4 wherein the cationic component is a natural or semi-synthetic peptide.

17. The formulation as claimed in claim 16 wherein the peptide is a protamine, gelatine, fibrinopeptide, or derivatives thereof.

18. The formulation as claimed in claim 4 wherein the cationic component is an aminoglucan or derivatives thereof.

19. The formulation as claimed in claim 18 wherein the aminoglucan is fractionated chitin or its de-acetylated derivative chitosan.

20. The formulation as claimed in claim 18 wherein the aminoglucan is of microbial origin or is isolated from the shells of arthropods such as crabs.

21. The formulation as claimed in claim 4 wherein the anionic component is polyanhydroglucuronic acid, or biocompatible salts thereof, or copolymers thereof.

22. The formulation as claimed in claim 3 wherein the polyanhydroglucuronic acid and salts thereof contain in their polymeric chain from 8 to 30 percent by weight of carboxyl groups, wherein at least 80 percent by weight of said carboxyl groups are of the uronic type, at most 5 percent by weight of said carboxyl groups are carbonyl groups, and at most 0.5 percent by weight of said carboxyl groups are bound nitrogen.

23. The formulation as claimed in claim 22 wherein the polyanhydroglucuromc acid and salts thereof contain in their polymeric chain at most 0.2 percent by weight of bound nitrogen.

24. The formulation as claimed in claim 22 wherein the molecular mass of the polymeric chain of the anionic component is from $1 \times 10^3$ to $3 \times 10^5$ Daltons.

25. The formulation as claimed in claim 24 wherein the molecular mass of the polymeric chain of the anionic component is from $5 \times 10^3$ to $1.5 \times 10^5$ Daltons.

26. The formulation as claimed in claim 22 wherein the content of carboxyl groups is in the range of from 12 to 26 percent by weight, at least 95 percent of these groups being of the uronic type.

27. The formulation as claimed in claim 22 wherein the anionic component contains at most 1 percent by weight of carbonyl groups.

28. The formulation as claimed in claim 22 wherein the carbonyl groups are intra- and intermolecular 2,6 and 3,6 hemiacetals, 2,4-hemialdals and C2–C3 aldehydes.

29. The formulation as claimed in claim 4 wherein the cationic component is gelatin.

30. The formulation as claimed in claim 4 wherein the cationic component is chitosan.

31. The formulation as claimed in claim 1 including at least one biocompatible biologically active substance.

32. The formulation as claimed in claim 1 including at least one biologically acceptable adjuvant.

33. The formulation as claimed in claim 1 in a form for oral administration.

34. The formulation as claimed in claim 1 in the form of a tablet, pellet, capsule, granule, or microsphere.

35. The formulation as claimed in claim 3 wherein the polyanhydroglucuronic acid or biocompatible salts thereof are in particle form having a size of from 0.1 to 100 μm.

36. The formulation as claimed in claim 3 wherein the polyanhydroglucuronic acid or biocompatible salts thereof are made up of fibers of from 5 to 30μm in diameter and up to 30mm in length.

37. The formulation as claimed in claim 3 wherein the polyanhydroglucuronic acid is stable microdispersed or microfibrillar polyanhydroglucuronic acid, biocompatible salts thereof, or copolymer thereof.

38. The formulation claimed in claim 4 wherein the anionic component is microdispersed or microfibrillar polyanhydroglucuronic acid or biocompatible salts thereof, or copolymer thereof.

* * * * *